United States Patent [19]

Wortley et al.

[11] Patent Number: 5,009,636
[45] Date of Patent: Apr. 23, 1991

[54] DUAL-LUMEN CATHETER APPARATUS AND METHOD

[75] Inventors: Ronald W. Wortley; David C. Beattie, both of Salt Lake City, Utah

[73] Assignee: The Kendall Company, Boston, Mass.

[21] Appl. No.: 446,971

[22] Filed: Dec. 6, 1989

[51] Int. Cl.$^5$ .................................................. A61M 5/00
[52] U.S. Cl. ......................................... 604/43; 604/280
[58] Field of Search ............................. 604/27, 43–45, 604/280, 264, 4

[56] References Cited

U.S. PATENT DOCUMENTS

| | | | |
|---|---|---|---|
| Re. 31,873 | 4/1985 | Howes | 128/674 |
| 3,411,506 | 11/1968 | Velasco . | |
| 3,499,435 | 3/1970 | Rockwell et al. | 128/2.05 |
| 3,794,026 | 2/1974 | Jacobs . | |
| 3,817,241 | 6/1974 | Grausz . | |
| 3,848,602 | 11/1974 | Gutnick . | |
| 3,995,623 | 12/1976 | Blake et al. . | |
| 4,403,983 | 9/1983 | Edelman et al. | 604/43 |
| 4,451,252 | 5/1984 | Martin | 604/43 |
| 4,583,968 | 4/1986 | Mahurkar | 604/43 |
| 4,643,711 | 2/1987 | Bates | 604/43 |
| 4,692,141 | 9/1987 | Mahurkar | 604/43 |
| 4,753,640 | 6/1988 | Nichols et al. | 604/43 |
| 4,895,561 | 1/1990 | Mahurkar | 604/43 |

FOREIGN PATENT DOCUMENTS

| | | |
|---|---|---|
| 689333 | 11/1966 | Belgium . |
| 2024791 | 12/1971 | Fed. Rep. of Germany . |
| 2302165 | 7/1974 | Fed. Rep. of Germany . |
| 3211585 | 12/1983 | Fed. Rep. of Germany . |
| 1544767 | 11/1968 | France . |
| 2530958 | 2/1984 | France . |
| 81/03613 | 12/1981 | World Int. Prop. O. . |

Primary Examiner—Stephen C. Pellegrino
Assistant Examiner—Ralph H. Lewis
Attorney, Agent, or Firm—Workman, Nydegger & Jensen

[57] ABSTRACT

A dual lumen catheter apparatus and method. The apparatus has an elongated catheter body adapted for insertion into a vein or a fluid-containing body cavity of a patient such as the right atrium of a heart. The catheter body has a septum that runs longitudinally through the interior of the catheter body so as to divide the interior of the catheter into a first and a second lumen. The septum is offset from the longitudinal center axis of the catheter so that the cross-sectional area of the two lumens are of different sizes. The first lumen has a cross-sectional size that is relatively large so that a sufficient volumetric flow rate of blood that is to be oxygenated is able to flow by means of gravity drainage through the first lumen whereas the second lumen is smaller but is still sufficiently large so that an essentially equal volumetric flow rate of blood that has been oxygenated can be returned under pressure through the second lumen.

11 Claims, 2 Drawing Sheets

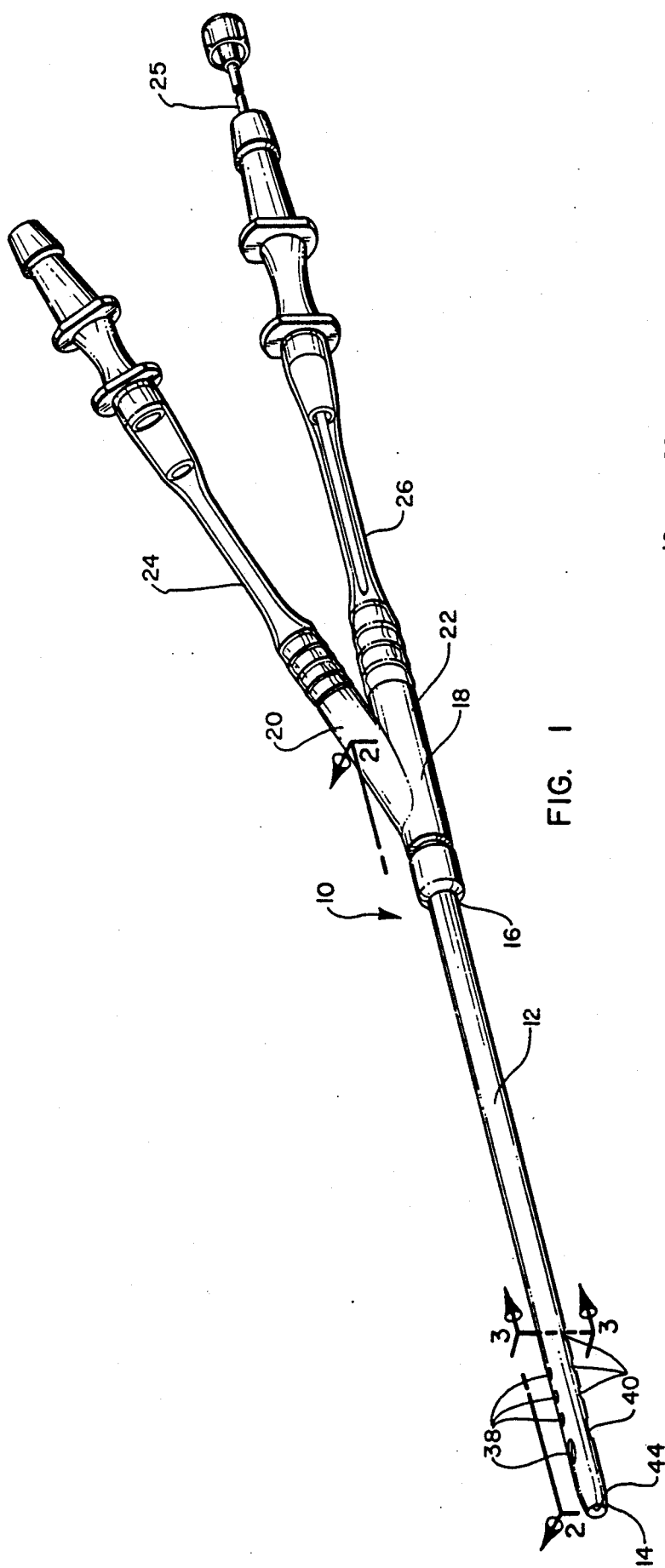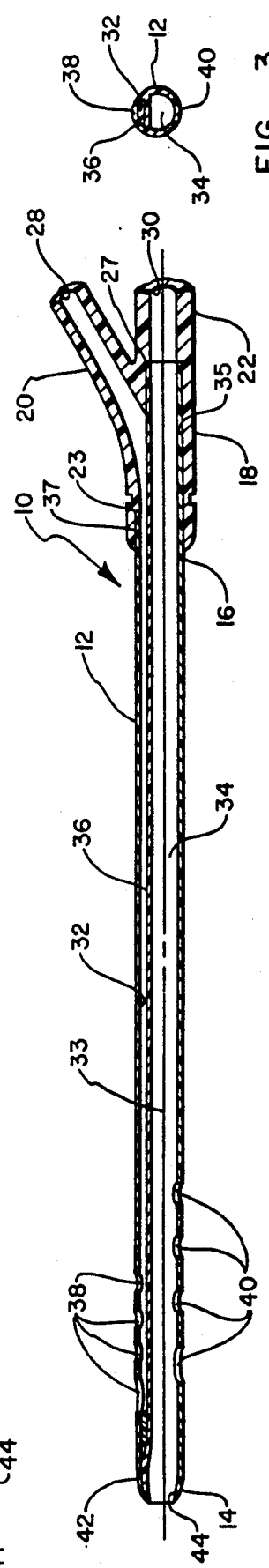

DUAL-LUMEN CATHETER APPARATUS AND METHOD

BACKGROUND

1. The Field of the Invention

The present invention relates to catheters and more particularly, the present invention is related to a dual-lumen catheter for use in extracorporeal oxygenation or other similar applications.

2. The Present State of the Art

In response to the need of patients with respiratory distress who fail to respond to conventional ventilatory management, many extracorporeal life support (ECLS) procedures and techniques have been developed to provide pulmonary and/or cardiac support for such patients. Extracorporeal membrane oxygenation (ECMO) is a life support technique which employs a cardiopulmonary bypass with a heart-lung machine to provide gas exchange, and to permit lungs to rest from damaging pressure and oxygen associated with conventional ventilation therapy. ECMO is often associated with neonatal respiratory dysfunction.

At the present time, two ECMO procedures are well known: venoarterial (VA) ECMO and venovenous (VV) ECMO. VA ECMO entails circulating the patient's blood through an extracorporeal system which pumps, oxygenates, and warms the blood. In order to withdraw the blood from the patient the right internal jugular vein is cannulated for venous drainage. The right common carotid artery is also cannulated for perfusion of the machine-oxygenated blood.

VV ECMO also entails circulating the patient's blood through an extracorporeal system which pumps, oxygenates and warms the blood. The distinction lies in the drainage and perfusion of blood. In VV ECMO, blood drainage is also accomplished by cannulation of the right jugular. However perfusion takes place in a vein rather than an artery. In VA ECMO, the perfusion of oxygenated blood is into the common carotid artery by employing a cannula placed in the common carotid artery at the level of the aortic arch. In VV ECMO, the perfusion of the oxygenated blood is into the femoral vein by employing a cannula secured in the femoral vein. This spares the common carotid artery.

In both VA and VV ECMO, the cannulation of the right jugular for drainage requires insertion of a catheter down the right jugular, into the superior vena cava, and into the right atrium of the heart. It is from the right atrium that blood drainage typically occurs in ECMO. Withdrawal of the blood from the right atrium is typically by gravity flow and the blood enters an extracorporeal circuit which oxygenates and warms the blood to suitable levels The extracorporeal circuit then pumps the oxygenated blood back into the patient for circulation in the body.

One drawback of both VA ECMO and VV ECMO is the necessary ligation of two primary veins and/or arteries. It is generally accepted that ligation poses the threat of future neurologic complications. Attempts to solve this problem have led to procedures involving a single ligation and cannulation, which use a tidal flow method (TF). In other words, the action of withdrawal and perfusion are mutually exclusive with respect to time through the same passage in a single cannula. While TF ECMO reduces the number of ligations from two to one it does not permit continuous and simultaneous withdrawal and perfusion of blood, and also results in recirculation of venous blood with oxygenated blood, since both withdrawal and return occur at the same site. Accordingly, it would be an important advance in the art to provide an apparatus and method which would permit the number of ligations necessary to provide ECLS to be reduced to one rather than two without being limited to a tidal flow method with its attendant disadvantages.

BRIEF SUMMARY AND OBJECTS OF THE INVENTION

The present invention resolves the above and other problems which have been experienced in the art and constitutes an important advance in the art of dual-lumen catheter systems, as evidenced by the following objects and advantages realized by the invention over the prior art.

One object of the present invention is a dual-lumen catheter which eliminates the necessity of ligating the common carotid artery or femoral vein typically required for perfusion of oxygenated blood in an ECMO system without being limited to the use of the present TF ECMO procedures.

Another object of the present invention is a dual-lumen catheter which permits the simultaneous venous drainage by gravity and perfusion at selected pressures of oxygenated blood necessary for successful ECMO procedures.

An additional object of the present invention is a dual-lumen catheter with a tip configuration such that drainage and perfusion of blood are not inhibited by surface tension.

Still an additional object of the present invention is a dual-lumen catheter having a tip configuration which minimizes recirculation by maximizing the control and direction of perfusion of oxygenated blood.

These and other objects and advantages of the invention will become more fully apparent from the description and claims which follow, or may be learned by the practice of the invention.

Briefly summarized, the foregoing objects are achieved by an apparatus which comprises an elongated catheter body that is adapted for insertion into a vein or fluid-containing body cavity of a patient, such as the right atrium of a heart. The catheter body comprises a septum that runs longitudinally through the interior of the catheter body so as to divide the interior of the catheter into a first and a second lumen. The septum is offset from the longitudinal center axis of the catheter so that the cross-sectional area of the two lumens are of different sizes. The first lumen has a cross section size which is relatively large so that a sufficient volumetric flow rate of blood that is to be oxygenated is able to flow by means of gravity drainage through the first lumen. The first lumen terminates in an opening at the distal end of the catheter and additional entry of blood into the first lumen occurs by means of a first plurality of longitudinally spaced openings formed through the wall of the catheter body.

The septum that runs through the catheter body is sealed near the distal end of the catheter body so that the second lumen terminates at a point that is slightly behind the distal end of the catheter Return of oxygenated blood under pressure occurs through the second lumen by means of a second plurality of holes that are longitudinally spaced and are formed through the catheter body diametrally opposite to the first plurality of openings. In this manner the withdrawal of blood that is to be oxygenated and the return of oxygenated blood is separated by the maximum distance so as to advantageously minimize the recirculation of venous blood with oxygenated blood. The cross-sectional of area the second lumen is sized so that at the selected pressure at which the oxygenated blood is returned, the volumetric flow rate of the blood through the second lumen will be essentially equal to the volumetric flow rate which occurs by means of gravity drainage through the first lumen.

Significantly, by means of the dual lumen catheter apparatus of the invention, only a single ligation is necessary in order to accomplish simultaneous withdrawal of venous blood and return of oxygenated blood.

BRIEF DESCRIPTION OF THE DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiment and the presently understood best mode of the invention will be described with additional detail through use of the accompanying drawings in which:

FIG. 1 is a perspective view of one presently preferred embodiment of the dual-lumen catheter of the present invention;

FIG. 2 is a longitudinal cross-section of the embodiment of FIG. 1 taken along lines 2—2, and more particularly illustrating the internal dual-lumen structure of the catheter;

FIG. 3 is a cross-section of the embodiment of FIG. 1 taken along lines 3—3, and illustrating the eccentric configuration of the two lumens.

DETAILED DESCRIPTION OF THE PREFERRED EMBODIMENTS

A. General Design Considerations

Figure 4:
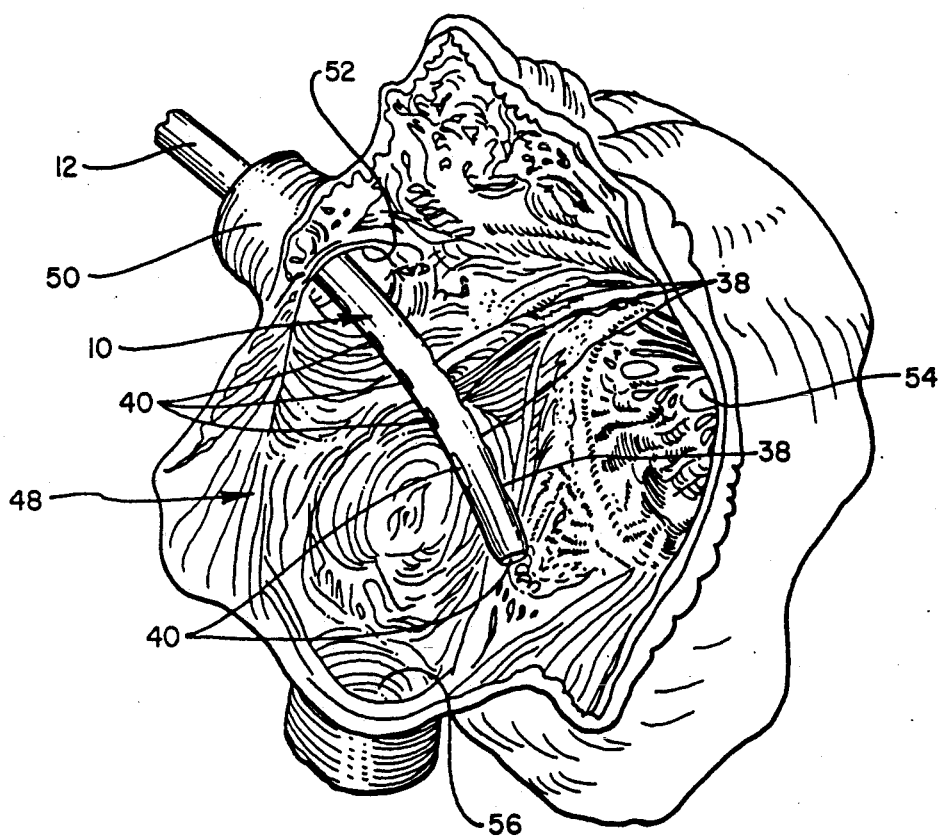
FIG. 4 is a perspective view of the position of the dual-lumen catheter in position in the right atrium of the heart with venous drainage occurring in the right atrium chamber and perfusion occurring by directing the flow of infusion in the direction of the tricuspid valve at the opening into the right ventricle.

Important objectives of any ECMO procedure include maintaining adequate venous drainage, oxygenation, and perfusion of the blood to compensate for any recirculation which might occur. Recirculation is a common occurrence when a fluid withdrawal/perfusion system such as ECMO takes place in a spherical structure such as the right atrium. Preferably, however, the venous, or oxygen depleted blood is not recirculated through the body with oxygenated blood. Therefore, a single catheter system must be so configured such that venous blood is effectively withdrawn from the patient without permitting impermissibly large quantities of oxygen depleted blood to reenter the circulatory system of the patient for another pass through the body. As a result, the withdrawal and perfusion functions of the catheter or cannula must be designed so that clinically permissible levels of recirculation are not exceeded.

A practical limitation of the size of any ECMO catheter is the size of the artery or vein in which the catheter is placed. For example, in a newborn a number 14 fr catheter is the largest catheter that will pass through the newborn's jugular enroute to the right atrium for venous drainage. The jugular of a larger child, adolescent, or adult would naturally, tolerate a proportionately larger catheter.

A critical aspect of ECMO techniques is the requisite quantity of blood flow from and to the patient. The configuration of the lumen withdrawing blood and the lumen perfusing blood must be of sufficient size, configuration and location so as to contribute to effective ECMO. For example, in order to provide adequate venous drainage, and in order to do so employing gravity suction (approximately 100–120 cm of syphon) while attaining a volumetric flow rate sufficient for oxygenation of approximately 500 cc/min. for a newborn and up to 5 l/min. for an adult, the drainage lumen must be of a relatively large size to provide such volumetric flow rates by means of gravity drainage.

Similarly, the lumen employed to perfuse the machine-oxygenated blood must also permit a volumetric flow rate compatible with the required ECMO blood flow levels and with the care necessary to avoid damaging the blood. Because blood is reinfused under pressure from the pump of the ECMO circuit, the size and configuration of the perfusion lumen may be smaller than the gravity drainage lumen. However, there are practical limitations to the pressure at which blood may be reinfused.

In order to avoid traumatizing the blood, the reinfusion pressure must be kept in a preferred range. For example, if reinfusion pressure exceeds 300–400 mm Hg, the blood becomes traumatized and breaks down. In order to prevent traumatization of the blood, it is desired to maintain the pressure of reinfusion at approximately 250 mm Hg. In addition, a certain volumetric flow rate of perfusion is needed, typically equal to the volumetric rate of withdrawal.

While gravity venous drainage must attain a certain volumetric flow rate, thus requiring an appropriately configured drainage lumen, and while reinfusion takes place under pressure and must return to the body the requisite volumetric flow rate, thus requiring a certain size or configuration of the perfusion lumen, the combined cross-sectional area of the two lumens may not exceed the practical limitation of the size of the vein or artery in which the catheter is placed or through which the catheter or cannula must pass.

The distal end of the catheter must be configured so as not to traumatize the vessel walls into which the catheter is placed or through which it must pass. In this respect the tip of the catheter is generally tapered and rounded, avoiding sharp or abrupt edges. If the tip of the catheter has an opening, the opening must not be so small that surface tension around the opening inhibits the required flow capacity of the catheter system. Therefore, it is necessary to configure the distal end of the catheter so that the flow of blood into the distal end of the catheter is not inhibited by surface tension.

Another desired function of the catheter apparatus is prevention of oxygenated blood from merely staying in the ECMO circuit cycle. The catheter should, to the extent possible, maximize the circulation of oxygenated blood and inhibit the oxygenated blood from reentering the extracorporeal circuit before it has passed through the patient Therefore, the distal end of the catheter must be configured such that the function of withdrawing blood and perfusing blood while occurring in relatively close proximity nonetheless are sufficiently located and spaced apart so as to avoid recirculation and reoxygenation of oxygenated blood. In other words, the configuration of the distal end of the catheter should permit the withdrawal of venous blood, and simultaneously control the direction and/or flow of perfused, oxygenated blood so that clinically permissible levels of recirculation are not exceeded and sufficient quantities of oxygenated blood are introduced into the patient for circulation through the patient's body.

B. Description of the Embodiment of Figures 1–5

The following detailed description of the presently preferred embodiment of the invention as illustrated for example, in FIGS. 1-5 illustrates how the general design considerations of the invention as described above, may be implemented. In the drawing figures like parts have been designated with like numerals throughout.

Reference is first made to FIG. 1 which illustrates a perspective view of the presently preferred embodiment. The catheter apparatus is generally designated at 10 and is comprised of an elongated catheter body 12 which terminates at its distal end 14 in a rounded tip and which is attached at its proximal end 16 to a Y connector 18. Distal end 14 of the elongated catheter body 12 is rounded and slightly tapered, as shown best in FIG. 2, so as to minimize the possibility of damaging delicate vessel walls or tissue walls as the catheter is inserted into the right atrium of the heart, as hereinafter more fully described in connection with FIGS. 4 and 5.

With continued reference to FIGS. 1 and 2 taken together, it will be seen that the elongated catheter body 12 is comprised of a septum means for forming a first and a second lumen through the interior of the catheter body. In the illustrated embodiment, the septum means for forming the first and second lumens is illustrated as a septum 36 (see FIG. 2) which runs lengthwise through the catheter body and which is offset from the longitudinal center axis 33 of the catheter body so as to define a first lumen 34 and a second, smaller lumen 32. As shown best in FIG. 3, the first lumen 34 is substantially larger in its cross-sectional area than the second lumen 32. The cross-sectional area of the first lumen 34 is sized so as to permit a sufficient volumetric flow rate for purposes of oxygenation of blood as the blood flows through the first lumen 34 by means of gravity drainage. The blood is permitted to enter into the first lumen 34, as shown best in FIG. 2, through the opening 44 at the distal end of the catheter body 12 and also through the longitudinally spaced openings 40 which are located on one side of the catheter body 12.

The second, smaller lumen 32 is substantially smaller in its cross-sectional shown area, as in FIG. 3, than the first lumen 34. The second lumen 32 is used for return of blood after it has been oxygenated. Since the blood is returned by means of a blood pump the blood returning through the second lumen 32 is pressurized and accordingly the cross-sectional area of the second lumen 32, although smaller than the cross-sectional area of the lumen 34 is nonetheless sized so that the volumetric flow rate of the blood which is returned under pressure is essentially equal to the volumetric flow rate of the blood which is being withdrawn by gravity drainage through the first lumen 34. The blood exists from the second lumen 32 by means of the openings 38 which are provided near the distal end of the catheter body 12. For purposes to be hereinafter more fully explained, the openings 38 through which the blood is returned is positioned on the catheter body 12 diametrally opposite to the openings 40 so that there is a maximum separation between the return openings 38 and the openings 40 through which blood is withdrawn. As will become more apparent in connection with FIGS. 4 and 5, this arrangement serves to minimize recirculation and helps to maximize the control and direction of perfusion of the oxygenated blood so that it is not withdrawn back into the catheter apparatus and recirculated for further oxygenation.

While the relative sizes of the first and second lumens 34 and 32 may vary somewhat, ultimately the relationship between the size of the two lumens will be governed by the overall size of the vessel for which the catheter apparatus is to be used. For example as noted above in the general design considerations, a volumetric flow rate sufficient for oxygenation for a newborn would typically be approximately 500 cc per minute, and could range up to 5 liters per minute for an adult. Accordingly, the drainage lumen or first lumen 34 must be of a relatively large size to provide the required volumetric flow rate whereas the second or small return lumen 32 may be smaller since the blood is returned under pressure, while still achieving an essentially equal volumetric flow rate to that of the first lumen.

With further reference to FIG. 2, it will be seen that the septum 36 is sealed as indicated at 42 at the distal end of the catheter body so that the second or return lumen 32 terminates slightly behind the outlet 44 of the gravity drainage lumen 34. By this means the oxygenated blood is required to be returned through the openings 38 for purposes of directing the return flow of the oxygenated blood in a direction which is substantially displaced and is away from the openings 40 and 44 through which the blood that is to be oxygenated is withdrawn. This minimizes recirculation of the blood that is already oxygenated with the blood that is to be oxygenated.

With continued reference to FIGS. 1 and 2, it will be seen that the Y connector 18 which is attached at the proximal end of the catheter body is formed with two branches 20 and 22 which provide separate flow passageways which in turn connect to the two lumens 32 and 34, respectively. Thus as shown in FIG. 2 the gravity drainage lumen 34 is in fluid communication with the passageway 30 provided by branch 22 of the Y connector whereas the return lumen 32 is in fluid communication with the flow passageway 28 of branch 20 of the Y connector. As shown in the longitudinal cross-sectional illustration of FIG. 2, the septum 36 and the lower wall 35 of the catheter body 12 extend into the Y connector 18 a sufficient distance to abut against a diametrically reduced shoulder 27. The upper wall 37 of the catheter body 12 similarly abuts against a diametrically reduced shoulder 23 so that a proper orientation with respect to the two lumens can be easily obtained and so that the catheter body 12 can be quickly inserted into and properly oriented relative to the two connecting passageways 28 and 30 of the Y connector.

As shown best in FIG. 1, the two branches 20 and 22 of the Y connector are in turn connected to tubing 24 and 26 which is joined by other appropriate fittings to the blood oxygenation circuit (not shown). Accordingly as will be appreciated from the foregoing, the Y connector serves as a means for attaching the catheter body to the tubing of the blood oxygenation circuitry and comprises means forming a first passageway for connection to tubing through which blood that is to be oxygenated is withdrawn from the first lumen, and means forming a second passageway for connection to other tubing through which the oxygenated blood is returned through the second lumen.

An obturator 25 may optionally be used to retard blood flow through the drainage lumen 34 while the apparatus is being positioned in the heart, as described below. Once positioned, the obturator 25 is removed and tubing 26 is connected to the extracorporeal blood oxygenation circuit.

Figure 5:
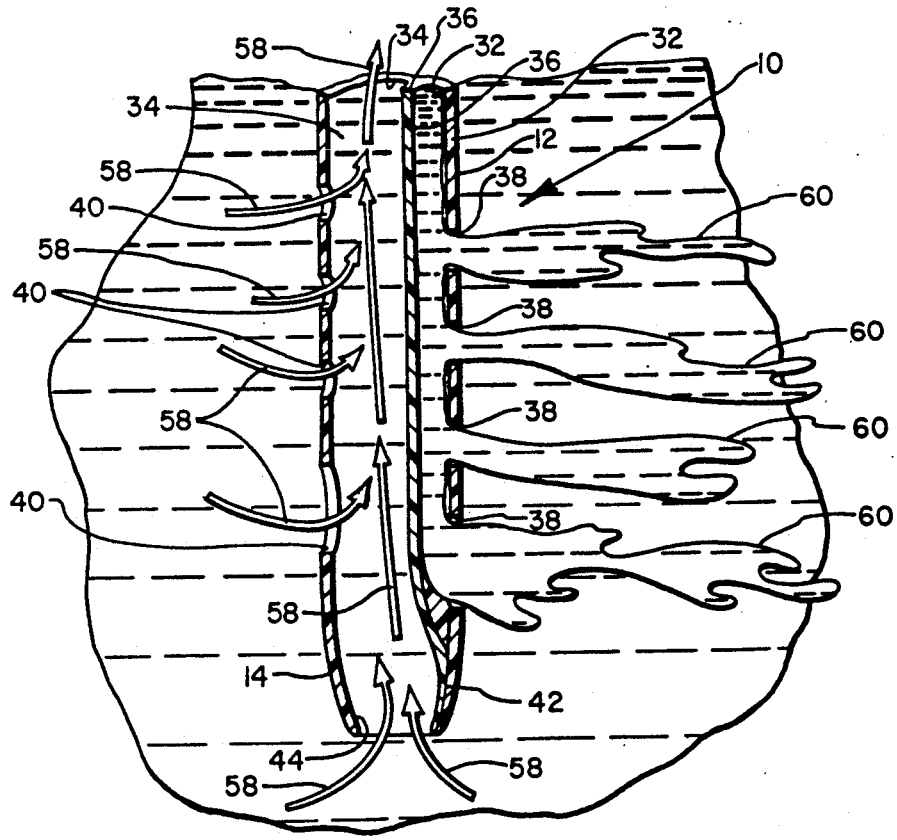
FIG. 5 is an enlarged cross-sectional view of the distal end of the dual-lumen catheter in position in the right atrium of the heart, and schematically illustrating the manner in which venous blood is withdrawn through a first lumen of the catheter while oxygenated blood is returned under pressure through the second lumen of the catheter in a manner which minimizes recirculation of the venous blood with the oxygenated blood.

Use of the catheter apparatus 10 in connection with extracorporeal oxygenation is illustrated in FIGS. 4 and 5. As shown in FIG. 4, the elongated catheter body 12 is passed through the superior vena cava 50 until the catheter body 12 passes through the opening of the superior vena cava 50 into the right atrium of the heart, which is generally designated at 48. Catheter body 12 is positioned such that the openings 40 through which blood is withdrawn by means of gravity drainage through the first lumen are directed in essentially the opposite direction from tricuspid valve 54 which is at the opening of the right ventricle of the heart.

As schematically illustrated in FIG. 5 by the arrows 58, blood enters through the opening 44 at the distal end of the catheter body and also through the openings 40 and flows through the first lumen 34 by means of gravity drainage. As further schematically illustrated in FIG. 5, once the oxygen-depleted blood has been circulated through the extracorporeal membrane oxygenation circuitry it is then returned under pressure through the return lumen 32. The openings 38 which communicate with the return lumen 32 are positioned essentially opposite to the openings 40 and are directed at the tricuspid valve 54. Since the blood that is oxygenated is returned under pressure, the blood is expelled with some force as schematically indicated at 60 so as to be directed toward the tricuspid valve 54. This serves to help in minimizing recirculation, although the pressure at which the blood is returned must be maintained within adequate levels so as not to traumatize the blood, as noted perviously From the foregoing, it will be appreciated that a substantial advantage of the catheter apparatus of the invention is that by means of a single catheter which requires only a single ligation both venous drainage and perfusion of oxygenated blood is accomplished. The catheter of the present invention also permits placement in the right atrium in a manner which is consistent with and enhances the natural circulatory flow of blood in the patient. In other words as will be appreciated, during normal circulation of blood oxygenated-depleted blood enters the right atrium through the opening of the superior vena cava and the inferior vena cava on its way to the right ventricle for subsequent reoxygenation. The catheter apparatus of the present invention specifically enhances and assists this type of normal circulation while doing so with only a single ligation.

The present invention may be embodied in other specific forms without departing from its spirit or essential characteristics and accordingly, the described embodiments are to be considered in all respects only as illustrative and not restrictive. The scope of the invention is, therefore, indicated by the appended claims rather than the foregoing description, and all changes which come within the meaning and range of equivalency of the claims are to be embraced within their scope.

What is claimed is:

1. An extracorporeal oxygenation catheter apparatus designed for simultaneous withdrawal of blood to be oxygenated by means of gravity drainage and pressurized return of blood that has been oxygenated, comprising:

an elongated catheter body having a distal end and a proximal end, and comprising a septum means for forming a first and a second lumen through the interior of said catheter body, said first lumen comprising a cross-sectional area sized so that a sufficient volumetric flow rate for purposes of oxygenation of said blood will occur in said first lumen as a result of gravity drainage of blood through the first lumen, and said second lumen comprising a cross-sectional area which is smaller in relation to said cross-sectional area of the first lumen but which is also sized so that a substantially equal volumetric flow rate of said oxygenated blood is returned under pressure through said second lumen, each said lumen comprising an opening means for passage of blood therethrough at said stated volumetric flow rate; and connector means joined to said proximal end for attaching said catheter body to tubing, said connector means comprising means forming a first passageway for connection to tubing through which said blood to be oxygenated is withdrawn from said first lumen, and means forming a second passageway for connection to other tubing through which said oxygenated blood is returned to said second lumen.

2. An apparatus as defined in claim 1 wherein said septum means for forming said first and second lumens comprises a septum which runs lengthwise through said catheter body, said septum being offset from the longitudinal center axis of said catheter body so as to define said cross-sectional areas.

3. An apparatus as defined in claim 2 wherein said septum is sealed to said catheter body at an interior wall thereof near said distal end of the catheter body, whereby said second lumen terminates at a point that is longitudinally displaced from said distal end.

4. An apparatus as defined in claims 1 or 3 wherein said apparatus further comprises a first plurality of longitudinally spaced openings formed on said catheter body and through which said blood to be oxygenated enters into said first lumen, and a second plurality of longitudinally spaced openings formed on said catheter body essentially diametrally opposite to said first plurality of openings and through which return of said oxygenated blood from said second lumen occurs, whereby blood to be oxygenated enters said catheter body on one side thereof and oxygenated blood is returned from said catheter body at an essentially opposite side thereof so as to maximize separation between blood that is withdrawn from oxygenated blood that is returned.

5. An apparatus as defined in claims 1 or 3 wherein said distal end of said catheter body is tapered, rounded and comprises an opening which communicates with said first lumen.

6. In an improved dual lumen catheter apparatus having an elongated catheter body with a tapered distal end for insertion into a vessel or fluid-containing cavity of a patient, and having a connector means attached at a proximal end of said catheter body for providing separate connection to and fluid communication through each said lumen, the improvement comprising:
- a septum disposed within said catheter body and running lengthwise therethrough, said septum being offset from the longitudinal center axis of said catheter body so as to define a first lumen having a cross-sectional area sized to permit a selected volumetric flow rate of fluid to occur therethrough by means of gravity drainage, and so as to define a second relatively smaller lumen having a cross-sectional area sized to permit a substantially equal volumetric flow rate of fluid to be returned through said second lumen at a selected pressure and;
- a first plurality of longitudinally spaced openings formed on said catheter body and through which said fluid enters into said first lumen, and a second plurality of longitudinally spaced openings formed on said catheter body essentially diametrally opposite to said first plurality of openings and through which return of said fluid from said second lumen occurs, whereby fluid enters said catheter body on one side thereof and is returned from said catheter body at an essentially opposite side thereof so as to maximize separation between fluid that is withdrawn from fluid that is returned.

7. An improved apparatus as defined in claim 6 wherein said septum is sealed to said catheter body at an interior wall thereof near said distal end of the catheter body, whereby said second lumen terminates at a point that is longitudinally displaced from said distal end.

8. An improved apparatus as defined in claims 6 or 7 wherein said distal end of said catheter body is tapered, rounded and comprises an opening which communicates with said first lumen.

9. An extracorporeal oxygenation catheter apparatus designed for simultaneous withdrawal of blood to be oxygenated by means of gravity drainage and pressurized return of blood that has been oxygenated, comprising:
- an elongated catheter body having a distal end and a proximal end, and comprising a septum disposed within said catheter body and running lengthwise therethrough, said septum being offset from the longitudinal center axis of said catheter body so as to define a first lumen having a cross-sectional area sized to permit a sufficient volumetric flow rate of said blood to occur in said first lumen as a result of gravity drainage of blood therethrough, for purposes of oxygenation and so as to define a second, relatively smaller lumen having a cross-sectional area sized to permit a substantially equal volumetric flow rate of oxygenated blood to be returned under pressure through said second lumen said septum being sealed to said catheter body at an interior wall thereof near the distal end of said catheter body so that said second lumen terminates at a point that is longitudinally displaced from said distal end, and said catheter body comprising a first plurality of longitudinally spaced openings placed near said distal end and through which said blood to be oxygenated enters into said first lumen, and a second plurality of longitudinally spaced openings formed on said catheter body essentially diametrally opposite to said first plurality of openings and through which return of said oxygenated blood from said second lumen occurs, whereby blood to be oxygenated enters said catheter body on one side thereof and oxygenated blood is returned from said catheter body at an essentially opposite side thereof in order to maximize separation between blood that is withdrawn from oxygenated blood that is returned; and
- a connector joined to said proximal end of said catheter body, said connector comprising a first branch forming a first passageway for connection to tubing through which said blood to be oxygenated is withdrawn from said first lumen, and comprising a second branch forming a second passageway for connection to other tubing through which said oxygenated blood is returned to said second lumen.

10. A method of extracorporeal blood oxygenation and return of blood that has been oxygenated, comprising the steps of:
- withdrawing said blood to be oxygenated by gravity drainage through a first lumen formed by a septum in the interior of a catheter body and having a first cross-sectional area sized so that a sufficient volumetric flow rate for purposes of oxygenation will occur by means of said gravity drainage; and
- returning said oxygenated blood under pressure through a second lumen formed by said septum in the interior of said catheter body adjacent to said first lumen, said return of oxygenated blood occurring at a volumetric flow rate that is substantially equal to said selected volumetric flow rate through said first lumen.

11. A method as defined in claim 10 wherein:
- said withdrawing step comprises withdrawing said blood to be oxygenated through a first plurality of openings formed on said catheter body; and
- said returning step comprises returning said oxygenated blood through a second plurality of openings formed on said catheter body essentially diametrally opposite from said first plurality of openings, whereby blood to be oxygenated enters said catheter body on one side thereof and oxygenated blood is returned from said catheter body at an essentially opposite side thereof so as to maximize separation between blood that is withdrawn from oxygenated blood that is returned.

* * * * *

UNITED STATES PATENT AND TRADEMARK OFFICE
CERTIFICATE OF CORRECTION

PATENT NO. : 5,009,636

DATED : April 23, 1991

INVENTOR(S) : RONALD W. WORTLEY et al.

It is certified that error appears in the above-identified patent and that said Letters Patent is hereby corrected as shown below:

```
Column 1, line 40, after "is" insert --pumped--
Column 1, line 43, after "is" insert --pumped--
Column 1, line 54, after "levels" insert --.--
Column 1, line 60, "neurologic" should be --neurological--
Column 2, line 64, after "catheter" insert --.--
Column 3, line 5, "of area" should be --area of--
Column 5, line 9, after "patient" insert --.--
Column 6, line 8, "exists" should be --exits--
Column 7, line 53, "perviously" should be --previously--
```

Signed and Sealed this

Twenty-third Day of March, 1993

Attest:

STEPHEN G. KUNIN

*Attesting Officer*     *Acting Commissioner of Patents and Trademarks*